United States Patent [19]
Tseriotis et al.

[11] Patent Number: 6,124,356
[45] Date of Patent: Sep. 26, 2000

[54] FUNGICIDES

[75] Inventors: George Tseriotis, Maidenhead; Ian Henry Aspinall, Sanohurst; Paul Anthony Worthington, Maidenhead, all of United Kingdom

[73] Assignee: Zeneca Limited, United Kingdom

[21] Appl. No.: 09/214,625

[22] PCT Filed: Jun. 27, 1997

[86] PCT No.: PCT/GB97/01729

§ 371 Date: Jan. 6, 1999

§ 102(e) Date: Jan. 6, 1999

[87] PCT Pub. No.: WO98/04520

PCT Pub. Date: Feb. 5, 1998

[30] Foreign Application Priority Data

Jul. 26, 1996 [GB] United Kingdom ............... 9615790

[51] Int. Cl.[7] ............ A01N 37/12; A01N 43/06; A01N 43/08; A01N 43/59
[52] U.S. Cl. .......... 514/538; 514/256; 514/357; 514/438; 514/471; 514/615; 544/335; 546/332; 549/77; 549/495; 549/496; 560/34; 560/35; 564/149; 564/150
[58] Field of Search ............... 514/256, 357, 514/438, 471, 538, 615; 544/335; 546/332; 549/77, 495, 496; 560/34, 35; 564/149, 150

[56] References Cited

FOREIGN PATENT DOCUMENTS

93/16986 9/1993 WIPO .
94/14322 7/1994 WIPO .

*Primary Examiner*—Peter O'Sullivan
*Attorney, Agent, or Firm*—Thomas R. Savitsky

[57] ABSTRACT

A fungicidal compound of formula (I): or a stereoisomer thereof, wherein A is CH or N, B is $OCH_3$ or $NHCH_3$, E is $—NR^1—C(CH_3)=N—$ or $—N=C(CH_3)—NR^1—$, $R^1$ is H, $C_{1-4}$ alkyl, $C_{2-4}$ alkenyl, $C_{2-4}$ alkynyl or optionally substitute benzyl, $R^2$ is H, $C_{1-4}$ alkyl, halo($C_{1-4}$)alkyl, $C_{3-6}$ cycloalkyl, $C_{2-4}$ alkenyl or $C_{2-4}$ alkynyl, and $R^3$ is optionally substituted aryl or optionally substituted heterocyclyl.

(I)

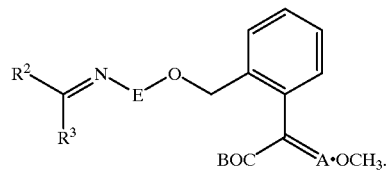

11 Claims, No Drawings

FUNGICIDES

This application is a 371 of PCT/GB97/01729 filed Jun. 1997.

The present invention relates to oxime derivatives, to a process for preparing them, to compositions containing them and to methods of using them to combat fungi, especially fungal infections of plants.

Certain oxime derivatives and their use as fungicides are described, for example, in WO93/16986 and WO94/14322.

According to the present invention there is provided a compound having the general formula (I):

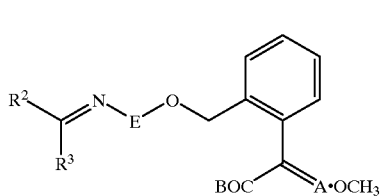

(I)

or a stereoisomer thereof, wherein A is CH or N, B is $OCH_3$ or $NHCH_3$, E is $-NR^1-C(CH_3)=N-$ or $-N=C(CH_3)-NR^1-$, $R^1$ is H, $C_{1-4}$ alkyl, $C_{2-4}$ alkenyl, $C_{2-4}$ alkynyl or optionally substituted benzyl, $R^2$ is H, $C_{1-4}$ alkyl, halo($C_{1-4}$)alkyl, $C_{3-6}$ cycloalkyl, $C_{2-4}$ alkenyl or $C_{2-4}$ alkynyl, and $R^3$ is optionally substituted aryl or optionally substituted heterocyclyl. More particularly, $R^3$ is a phenyl or heterocyclyl moiety optionally substituted by one or more of halogen, hydroxy, mercapto, $C_{1-4}$ alkyl (especially methyl and ethyl), $C_{2-4}$ alkenyl (especially allyl), $C_{2-4}$ alkynyl (especially propargyl), $C_{1-4}$ alkoxy (especially methoxy), $C_{2-4}$ alkenyloxy (especially allyloxy), $C_{2-4}$ alkynyloxy (especially propargyloxy), halo($C_{1-4}$)alkyl (especially trifluoromethyl), halo($C_{1-4}$)alkoxy (especially trifluoromethoxy), $C_{1-4}$ alkylthio (especially methylthio), hydroxy($C_{1-4}$)alkyl, $C_{1-4}$ alkoxy($C_{1-4}$)alkyl, $C_{3-6}$ cycloalkyl, $C_{3-6}$ cycloalkyl($C_{1-4}$)alkyl, optionally substituted methylenedioxy (especially optionally substituted with fluorine or $C_{1-4}$ alkyl), optionally substituted aryl (especially optionally substituted phenyl), optionally substituted heteroaryl (especially optionally substituted pyridyl or pyrimidinyl), optionally substituted saturated or partially saturated heterocyclyl (especially optionally substituted pyrrolidine), optionally substituted aryloxy (especially optionally substituted phenoxy), optionally substituted heteroaryloxy (especially optionally substituted pyridyloxy or pyrimidinyloxy), optionally substituted aryl($C_{1-4}$)alkyl (especially optionally substituted benzyl, optionally substituted phenethyl and optionally substituted phenyl n-propyl) in which the alkyl moiety is optionally substituted with hydroxy, optionally substituted heteroaryl($C_{1-4}$)alkyl (especially optionally substituted pyridyl- or pyrimidinyl($C_{1-4}$)alkyl), optionally substituted aryl($C_{2-4}$)alkenyl (especially optionally substituted phenylethenyl), optionally substituted heteroaryl($C_{2-4}$)alkenyl (especially optionally substituted pyridylethenyl or pyrimidinylethenyl), optionally substituted aryl($C_4$)alkoxy (especially optionally substituted benzyloxy), optionally substituted heteroaryl ($C_{1-4}$)alkoxy (especially optionally substituted pyridyl- or pyrimidinyl($C_{1-4}$)alkoxy), optionally substituted aryloxy($C_{1-4}$)alkyl (especially phenoxymethyl), optionally substituted heteroaryloxy($C_{1-4}$)alkyl (especially optionally substituted pyridyloxy- or pyrimidinyloxy($C_{1-4}$)alkyl), acyloxy (including $C_{1-4}$ alkanoyloxy (especially acetyloxy) and benzoyloxy), nitro, $-NR'R''$, $-NHCOR'$, $-NHCONR'R''$, $-CONR'R''$, $-OSO_2R'$, $-SO_2R'$, $-COR'$, $-CR'=NR''$ or $-N=CR'R''$ in which R' and R'' are independently hydrogen, $C_{1-4}$ alkyl, $C_{1-4}$ alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy, or R' and R'' in CONR'R'' may, in addition, form together a 5- or 6-membered heterocyclic ring (for example a pyrrole, imidazole, pyrrolidine, piperidine or morpholine ring); or two substituents, when they are in adjacent positions on the aryl or heteroaryl ring, join to form a fused aliphatic ring (especially a fused 6-membered carbon aliphatic ring).

Substituents which may be present in the aryl or heteroaryl rings of any of the foregoing substituents, or in the phenyl ring when $R^1$ is optionally substituted benzyl, include one or more of the following: halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$)alkyl, halo($C_{1-4}$)alkoxy, $C_{1-4}$ alkylthio, hydroxy($C_{1-4}$)alkyl, $C_{1-4}$ alkoxy ($C_{1-4}$)alkyl, $C_{3-6}$ cycloalkyl, $C_{3-6}$ cycloalkyl($C_{1-4}$)alkyl, alkanoyloxy, benzoyloxy, nitro, $-NR'R''$, $-NHCOR'$, $-NHCONR'R''$, $-CONR'R''$, $-SO_2R'$, $-OSO_2R'$, $-COR'$, $-CR'NR''$ or $-N=CR'R''$ in which R' and R'' have the meanings given above.

Of particular interest are those compounds where $R^1$ is H or methyl, especially H, $R^2$ is H, cyclopropyl or, preferably, methyl, and $R^3$ is as defined above. Preferably A is N and B is $OCH_3$ or $NHCH_3$ and, more preferably, A is CH and B is $OCH_3$.

Owing to the presence of the three double bonds, the compounds may be obtained in the form of mixtures of (E)- and (Z)-geometric isomers. However, these mixtures can be separated into individual isomers, and this invention embraces such isomers and mixtures thereof in all proportions. The (E)-isomers with respect to the group $BOC.C=A.OCH_3$ are s usually the more fungicidally active and form a preferred embodiment of the invention.

Optionally substituted methylenedioxy includes $-OCH_2O-$, $-OCHFO-$, $-OCF_2O$, $-OCH(CH_3)O-$ and $-OC(CH_3)_2O-$.

Aryl is preferably phenyl, but also includes, for example, naphthyl.

Heteroaryl includes 5- and 6-membered aromatic rings containing one or more heteroatoms selected from the list comprising oxygen, sulphur and nitrogen and can be fused to benzenoid ring systems. Examples of heteroaryl are pyridinyl, pyrimidinyl, pyridazinyl, pyrazinyl, triazinyl, furyl, thienyl, pyrrolyl, pyrazolyl, imidazolyl, triazolyl, oxazolyl, isoxazolyl, thiazolyl, isothiazolyl, quinolinyl, isoquinolinyl, cinnolinyl, quinazolinyl, quinoxalinyl, indolinyl, isoindolinyl, benzofuranyl, benzthiazolyl, benzothiophenyl and benzimidazolinyl.

Heterocyclyl includes heteroaryl as previously defined and also includes non-aromatic rings such as pyrrolidine, morpholine and piperidine.

Alkyl moieties and the alkyl moiety of alkoxy and haloalkyl preferably contain, unless otherwise stated, from 1 to 4 carbon atoms. They can be in the form of straight or branched chains. Examples are methyl, ethyl, n- or iso-propyl, or n-, sec-, iso- or tert-butyl.

Alkenyl and alkynyl moieties preferably contain, unless otherwise stated, from 2 to 4 carbon atoms. They can be in the form of straight or branched chains, and the alkenyl moieties, where appropriate, may have either the (E)- or (Z)-configuration. Examples are vinyl, allyl and propargyl.

Halogen is typically fluorine, chlorine or bromine.

It is preferred that $R^1$ is hydrogen or $C_{1-4}$ alkyl (especially methyl). Compounds wherein $R^1$ is hydrogen form a more preferred embodiment of the present invention.

It is preferred that $R^2$ is methyl.

In one aspect, the present invention provides a compound of formula (I), wherein A is CH, B is $OCH_3$, $R^1$ is H or $CH_3$, $R^2$ is $CH_3$ and $R^3$ is phenyl optionally substituted (i.e. unsubstituted or substituted with, for example, 1, 2 or 3 substituents) with halogen (such as fluorine or chlorine), $C_{1-4}$ alkyl (such as methyl), $C_{2-4}$ alkenyl (such as vinyl or allyl), $C_{2-4}$ alkynyl (such as propargyl), $C_{1-4}$ alkoxy (such as methoxy or ethoxy), $C_{2-4}$ alkenyloxy (such as allyloxy), $C_{2-4}$ alkynyloxy (such as propargyloxy), halo($C_{1-4}$)alkyl (such as $CF_3$), halo($C_{1-4}$)alkoxy (such as $OCF_3$), $C_{1-4}$-alkoxy($C_{1-4}$)alkyl (such as methoxymethyl), acyloxy (such as acetyloxy or benzoyloxy), nitro, —NR'R", —NHCOR', —CONR'R" or COR' in which R' and R" are independently hydrogen, $C_{1-4}$ alkyl or $C_{1-4}$ alkoxy.

In another aspect the present invention provides a compound of formula (I), wherein A is CH, B is $OCH_3$, $R^1$ is H or $CH_3$, $R^2$ is $CH_3$ and $R^3$ is phenyl optionally substituted with halogen (especially chlorine or fluorine), $C_{1-4}$ alkyl, halo($C_{1-4}$)alkyl (such as $CF_3$, $C_2F_5$, $CF_3CH_2$ or $CH_3CF_2$) $C_{1-4}$ alkoxy, halo($C_{1-4}$)alkoxy or nitro. Examples of $R^3$ are phenyl, 4-chlorophenyl, 2,4-difluorophenyl, 2-methylphenyl, 3-methylphenyl, 4-methylphenyl and 3-trifluoromethylphenyl.

The present invention is illustrated by compounds of formula (I) which are listed in Tables 1 to 15.

TABLE 1

Compounds in Table 1 are of general formula (I) wherein A is CH, B is $OCH_3$, E is —$NR^1$—C($CH_3$)=N—, $R^1$ is H, $R^2$ is methyl and $R^3$ has the value listed.

| Compound No | $R^3$ |
|---|---|
| 1. | $C_6H_5$ |
| 2. | 2-$CF_3$—$C_6H_4$ |
| 3. | 3-$CF_3$—$C_6H_4$ |
| 4. | 4-$CF_3$—$C_6H_4$ |
| 5. | 2-Cl—$C_6H_4$ |
| 6. | 3-Cl—$C_6H_4$ |
| 7. | 4-Cl—$C_6H_4$ |
| 8. | 2-$CH_3$—$C_6H_4$ |
| 9. | 3-$CH_3$—$C_6H_4$ |
| 10. | 4-$CH_3$—$C_6H_4$ |
| 11. | 2-$CH_3O$—$C_6H_4$ |
| 12. | 3-$CH_3O$—$C_6H_4$ |
| 13. | 4-$CH_3O$—$C_6H_4$ |
| 14. | 2-F—$C_6H_4$ |
| 15. | 3-F—$C_6H_4$ |
| 16. | 4-F—$C_6H_4$ |
| 17. | 2,3-$F_2$—$C_6H_3$ |
| 18. | 2,4-$F_2$—$C_6H_3$ |
| 19. | 2,5-$F_2$—$C_6H_3$ |
| 20. | 2,6-$F_2$—$C_6H_3$ |
| 21. | 3,4-$F_2$—$C_6H_3$ |
| 22. | 3,5-$F_2$—$C_6H_3$ |
| 23. | $C_6F_5$ |
| 24. | 2,3,4-$F_3$—$C_6H_2$ |
| 25. | 2,3,5-$F_3$—$C_6H_2$ |
| 26. | 2,3,6-$F_3$—$C_6H_2$ |
| 27. | 3,4,5-$F_3$—$C_6H_2$ |
| 28. | 2-Br—$C_6H_4$ |
| 29. | 3-Br—$C_6H_4$ |
| 30. | 4-Br—$C_6H_4$ |

TABLE 1-continued

Compounds in Table 1 are of general formula (I) wherein A is CH, B is $OCH_3$, E is —$NR^1$—C($CH_3$)=N—, $R^1$ is H, $R^2$ is methyl and $R^3$ has the value listed.

| Compound No | $R^3$ |
|---|---|
| 31. | 2-$NO_2$—$C_6H_4$ |
| 32. | 3-$NO_2$—$C_6H_4$ |
| 33. | 4-$NO_2$—$C_6H_4$ |
| 34. | 2,3-$Cl_2$—$C_6H_5$ |
| 35. | 2,4-$Cl_2$—$C_6H_5$ |
| 36. | 2,5-$Cl_2$—$C_6H_5$ |
| 37. | 2,6-$Cl_2$—$C_6H_5$ |
| 38. | 3,4-$Cl_2$—$C_6H_5$ |
| 39. | 3,5-$Cl_2$—$C_6H_5$ |
| 40. | $C_6Cl_5$ |
| 41. | 2,3,4-$Cl_3$—$C_6H_2$ |
| 42. | 2,4,6-$Cl_3$—$C_6H_2$ |
| 43. | 3,4,5-$Cl_3$—$C_6H_2$ |
| 44. | 2-$C_2F_5$—$C_6H_4$ |
| 45. | 3-$C_2H_5$—$C_6H_4$ |
| 46. | 4-$C_2H_5$—$C_6H_4$ |
| 47. | 2-$CCl_3$—$C_6H_4$ |
| 48. | 3-$CCl_3$—$C_6H_4$ |
| 49. | 4-$CCl_3$—$C_6H_4$ |
| 50. | 2-F-3-Cl—$C_6H_3$ |
| 51. | 2-Cl-3-F—$C_6H_3$ |
| 52. | 2-F-4-Cl—$C_6H_3$ |
| 53. | 2-Cl-4-F—$C_6H_3$ |
| 54. | 2-F-5-Cl—$C_6H_3$ |
| 55. | 2-Cl-5-F—$C_6H_3$ |
| 56. | 2-F-6-Cl—$C_6H_3$ |
| 57. | 2-F-5-Cl—$C_6H_3$ |
| 58. | 2-F-4-Cl—$C_6H_3$ |
| 59. | 3-Cl-4-Cl—$C_6H_3$ |
| 60. | 2-$CF_3CH_2$—$C_6H_4$ |
| 61. | 3-$CF_3CH_2$—$C_6H_4$ |
| 62. | 4-$CF_3CH_2$—$C_6H_4$ |
| 63. | 2-$CH_3CF_2$—$C_6H_4$ |
| 64. | 3-$CH_3CF_2$—$C_6H_4$ |
| 65. | 4-$CH_3CF_2$—$C_6H_4$ |
| 66. | 2-$CF_3(CF_2)_2$—$C_6H_4$ |
| 67. | 3-$CF_3(CF_2)_2$—$C_6H_4$ |
| 68. | 4-$CF_3(CF_2)_2$—$C_6H_4$ |
| 69. | 2-$(CF_3)_2CF$—$C_6H_4$ |
| 70. | 3-$(CF_3)_2CF$—$C_6H_4$ |
| 71. | 4-$(CF_3)_2CF$—$C_6H_4$ |
| 72. | 3-Methylbenzo[b]-thiopen-7-yl |
| 73. | Pyridin-2-yl |
| 74. | Pyridin-3-yl |
| 75. | Pyridin-4-yl |
| 76. | 3-Methylpyridin-2-yl |
| 77. | 4-Methylpyridin-2-yl |
| 78. | 5-Methylpyridin-2-yl |
| 79. | 6-Methylpyridin-2-yl |
| 80. | 2-Methylpyridin-3-yl |
| 81. | 4-Methylpyridin-3-yl |
| 82. | 5-Methylpyridin-3-yl |
| 83. | 6-Methylpyridin-3-yl |
| 84. | 2-Methylpyridin-4-yl |
| 85. | 3-Methylpyridin-4-yl |
| 86. | 4-Cyclopropyl-pyrimidin-2-yl |
| 87. | 4-Methyl-6-methoxy-pyrimidin-2-yl |
| 88. | 5-Chloropyrimidin-2-yl |
| 89. | 4,6-Dimethylpyrimidin-2-yl |
| 90. | 2-$CH_3OCH_2$—$C_6H_4$ |
| 91. | 3-$CH_3OCH_2$—$C_6H_4$ |
| 92. | 4-$CH_3OCH_2$—$C_6H_4$ |
| 93. | 2-$NH_2$—$C_6H_4$ |
| 94. | 3-$NH_2$—$C_6H_4$ |
| 95. | 4-$NH_2$—$C_6H_4$ |
| 96. | 2,3-$(CH_3)_2$—$C_6H_4$ |
| 97. | 2,4-$(CH_3)_2$—$C_6H_4$ |
| 98. | 2,5-$(CH_3)_2$—$C_6H_4$ |
| 99. | 2,6-$(CH_3)_2$—$C_6H_4$ |
| 100. | 2-$CH_3$-3-$NO_2$—$C_6H_3$ |
| 101. | 2-$CH_3$-4-$NO_2$—$C_6H_3$ |
| 102. | 2-$CH_3$-5-$NO_2$—$C_6H_3$ |

TABLE 1-continued

Compounds in Table 1 are of general formula (I) wherein A is CH, B is OCH$_3$, E is —NR$^1$—C(CH$_3$)=N—, R$^1$ is H, R$^2$ is methyl and R$^3$ has the value listed.

| Compound No | R$^3$ |
|---|---|
| 103. | 2-CH$_3$-6-NO$_2$—C$_6$H$_3$ |
| 104. | 3-CH$_3$-2-NO$_2$—C$_6$H$_3$ |
| 105. | 3-CH$_3$-4-NO$_2$—C$_6$H$_3$ |
| 106. | 3-CH$_3$-5-NO$_2$—C$_6$H$_3$ |
| 107. | 3-H$_3$-6-NO$_2$—C$_6$H$_3$ |
| 108. | 2-NO$_2$-4-CH$_3$—C$_6$H$_3$ |
| 109. | 3-NO$_2$-4-CH$_3$—C$_6$H$_3$ |
| 110. | 2-F-3-NO$_2$—C$_6$H$_3$ |
| 111. | 2-F-4-NO$_2$—C$_6$H$_3$ |
| 112. | 2-F-5-NO$_2$—C$_6$H$_3$ |
| 113. | 2-F-6-NO$_2$—C$_6$H$_3$ |
| 114. | 3-F-2-NO$_2$—C$_6$H$_3$ |
| 115. | 3-F-4-NO$_2$—C$_6$H$_3$ |
| 116. | 3-F-5-NO$_2$—C$_6$H$_3$ |
| 117. | 3-F-6-NO$_2$—C$_6$H$_3$ |
| 118. | 4-F-2-NO$_2$—C$_6$H$_3$ |
| 119. | 4-F-3-NO$_2$—C$_6$H$_3$ |
| 120. | 2-F-3-CF$_3$—C$_6$H$_3$ |
| 121. | 2-F-4-CF$_3$—C$_6$H$_3$ |
| 122. | 2-F-5-CF$_3$—C$_6$H$_3$ |
| 123. | 2-F-6-CF$_3$—C$_6$H$_3$ |
| 124. | 3-F-2-CF$_3$—C$_6$H$_3$ |
| 125. | 3-F-4-CF$_3$—C$_6$H$_3$ |
| 126. | 3-F-5-CF$_3$—C$_6$H$_3$ |
| 127. | 3-F-6-CF$_3$—C$_6$H$_3$ |
| 128. | 4-F-2-CF$_3$—C$_6$H$_3$ |
| 129. | 4-F-3-CF$_3$—C$_6$H$_3$ |
| 130. | 2-CH$_3$O-3-NO$_2$—C$_6$H$_3$ |
| 131. | 2-CH$_3$O-4-NO$_2$—C$_6$H$_3$ |
| 132. | 2-CH$_3$O-5-NO$_2$—C$_6$H$_3$ |
| 133. | 2-CH$_3$O-6-NO$_2$—C$_6$H$_3$ |
| 134. | 3-CH$_3$O-2-NO$_2$—C$_6$H$_3$ |
| 135. | 3-CH$_3$O-4-NO$_2$—C$_6$H$_3$ |
| 136. | 3-CH$_3$O-5-NO$_2$—C$_6$H$_3$ |
| 137. | 3-CH$_3$O-6-NO$_2$—C$_6$H$_3$ |
| 138. | 4-CH$_3$O-2-NO$_2$—C$_6$H$_3$ |
| 139. | 4-CH$_3$O-3-NO$_2$—C$_6$H$_3$ |
| 140. | 2-CH$_3$O-3-CF$_3$—C$_6$H$_3$ |
| 141. | 2-CH$_3$O-4-CF$_3$—C$_6$H$_3$ |
| 142. | 2-CH$_3$O-5-CF$_3$—C$_6$H$_3$ |
| 143. | 2-CH$_3$O-6-CF$_3$—C$_6$H$_3$ |
| 144. | 3-CH$_3$O-2-CF$_3$—C$_6$H$_3$ |
| 145. | 3-CH$_3$O-4-CF$_3$—C$_6$H$_3$ |
| 146. | 3-CH$_3$O-5-CF$_3$—C$_6$H$_3$ |
| 147. | 3-CH$_3$O-6-CF$_3$—C$_6$H$_3$ |
| 148. | 4-CH$_3$O-2-CF$_3$—C$_6$H$_3$ |
| 149. | 4-CH$_3$O-3-CF$_3$—C$_6$H$_3$ |
| 150. | 2-CH$_3$-3-CH$_3$—O—C$_6$H$_3$ |
| 151. | 2-CH$_3$-4-CH$_3$—O—C$_6$H$_3$ |
| 152. | 2-CH$_3$-5-CH$_3$—O—C$_6$H$_3$ |
| 153. | 2-CH$_3$-6-CH$_3$—O—C$_6$H$_3$ |
| 154. | 3-CH$_3$-3-CH$_3$O—C$_6$H$_5$ |
| 155. | 3-CH$_3$-4-CH$_3$O—C$_6$H$_5$ |
| 156. | 3-CH$_3$-5-CH$_3$O—C$_6$H$_5$ |
| 157. | 3-CH$_3$-6-CH$_3$O—C$_6$H$_5$ |
| 158. | 4-CH$_3$-2-CH$_3$O—C$_6$H$_5$ |
| 159. | 4-CH$_3$-3-CH$_3$O—C$_6$H$_5$ |
| 160. | 2-F-3-CH$_3$—C$_6$H$_3$ |
| 161. | 2-F-4-CH$_3$—C$_6$H$_3$ |
| 162. | 2-F-5-CH$_3$—C$_6$H$_3$ |
| 163. | 2-F-6-CH$_3$—C$_6$H$_3$ |
| 164. | 3-F-2-CH$_3$—C$_6$H$_3$ |
| 165. | 3-F-4-CH$_3$—C$_6$H$_3$ |
| 166. | 3-F-5-CH$_3$—C$_6$H$_3$ |
| 167. | 3-F-6-CH$_3$—C$_6$H$_3$ |
| 168. | 4-F-2-CH$_3$—C$_6$H$_3$ |
| 169. | 4-F-3-CH$_3$—C$_6$H$_3$ |
| 170. | 2-F-3-CH$_3$O—C$_6$H$_3$ |
| 171. | 2-F-4-CH$_3$O—C$_6$H$_3$ |
| 172. | 2-F-5-CH$_3$O—C$_6$H$_3$ |
| 173. | 2-F-6-CH$_3$O—C$_6$H$_3$ |
| 174. | 3-F-2-CH$_3$O—C$_6$H$_3$ |
| 175. | 3-F-4-CH$_3$O—C$_6$H$_3$ |
| 176. | 3-F-5-CH$_3$O—C$_6$H$_3$ |
| 177. | 3-F-6-CH$_3$O—C$_6$H$_3$ |
| 178. | 4-F-2-CH$_3$O—C$_6$H$_3$ |
| 179. | 4-F-3-CH$_3$O—C$_6$H$_3$ |
| 180. | 2-Cl-3-CH$_3$O—C$_6$H$_3$ |
| 181. | 2-Cl-4-CH$_3$O—C$_6$H$_3$ |
| 182. | 2-Cl-5-CH$_3$O—C$_6$H$_3$ |
| 183. | 2-Cl-6-CH$_3$O—C$_6$H$_3$ |
| 184. | 3-Cl-2-CH$_3$O—C$_6$H$_3$ |
| 185. | 3-Cl-4-CH$_3$O—C$_6$H$_3$ |
| 186. | 3-Cl-5-CH$_3$O—C$_6$H$_3$ |
| 187. | 3-Cl-6-CH$_3$O—C$_6$H$_3$ |
| 188. | 4-Cl-2-CH$_3$O—C$_6$H$_3$ |
| 189. | 4-Cl-3-CH$_3$O—C$_6$H$_3$ |
| 190. | 3,4-OCH$_2$O—C$_6$H$_3$ |
| 191. | 3,4-OC$_2$H$_4$O—C$_6$H$_3$ |
| 192. | 4-F-2-pyridinyl |
| 193. | 4-Cl-2-pyridinyl |
| 194. | 2-F-4-pyridinyl |
| 195. | 2-Cl-4-pyridinyl |
| 196. | 2-Cl-6-pyridinyl |
| 197. | 2-F-6-pyridinyl |
| 198. | 2-CF$_3$-6-pyridinyl |
| 199. | 4-CF$_3$-2-pyridinyl |
| 200. | 2-CH$_3$O-3-pyridinyl |
| 201. | 2-CH$_3$O-4-pyridinyl |
| 202. | 2-CH$_3$O-5-pyridinyl |
| 203. | 2-CH$_3$O-6-pyridinyl |
| 204. | 3-CH$_3$O-2-pyridinyl |
| 205. | 3-CH$_3$O-4-pyridinyl |
| 206. | 3-CH$_3$O-5-pyridinyl |
| 207. | 3-CH$_3$O-6-pyridinyl |
| 208. | 4-CH$_3$O-2-pyridinyl |
| 209. | 4-CH$_3$O-3-pyridinyl |
| 210. | 2,6-diF-3-pyridinyl |
| 211. | 6-Cl-2-pyrimidinyl |
| 212. | 5-F-2-pyrimidinyl |
| 213. | 5-CH$_3$-2-pyrimidinyl |
| 214. | 4-CH$_3$O-2-pyrimidinyl |
| 215. | 2-CH$_3$O-4-pyrimidinyl |
| 216. | 2-CH$_3$O-5-pyrimidinyl |
| 217. | 4-CH$_3$O-6-pyrimidinyl |
| 218. | 5-CH$_3$O-4-pyrimidinyl |
| 219. | 6-CH$_3$O-5-pyrimidinyl |
| 220. | 4-C$_2$H$_5$O-2-pyrimidinyl |
| 221. | 2-CF$_3$-4-pyrimidinyl |
| 222. | 4-CF$_3$-2-pyrimidinyl |
| 223. | 4-CF$_3$-5-pyrimidinyl |
| 224. | 4-CF$_3$-6-pyrimidinyl |
| 225. | 5-CF$_3$-6-pyrimidinyl |
| 226. | 4-CF$_3$CH$_2$O-2-pyrimidinyl |
| 227. | 6-CH$_3$O-2-benzthiazolyl |
| 228. | furan-2-yl |
| 229. | thien-2-yl |
| 230. | thien-3-yl |
| 231. | 2-CH$_3$S—C$_6$H$_4$ |
| 232. | 3-CH$_3$S—C$_6$H$_4$ |
| 233. | 4-CH$_3$S—C$_6$H$_4$ |
| 234. | 2-Cl-3-CH$_3$—C$_6$H$_3$ |
| 235. | 2-Cl-4-CH$_3$—C$_6$H$_3$ |
| 236. | 2-Cl-5-CH$_3$—C$_6$H$_3$ |
| 237. | 2-Cl-6-CH$_3$—C$_6$H$_3$ |
| 238. | 3-Cl-2-CH$_3$—C$_6$H$_3$ |
| 239. | 3-Cl-4-CH$_3$—C$_6$H$_3$ |
| 240. | 3-Cl-5-CH$_3$—C$_6$H$_3$ |
| 241. | 3-Cl-6-CH$_3$—C$_6$H$_3$ |
| 242. | 4-Cl-2-CH$_3$—C$_6$H$_3$ |
| 243. | 4-Cl-3-CH$_3$—C$_6$H$_3$ |
| 244. | 2-Cl-3-NO$_2$—C$_6$H$_3$ |
| 245. | 2-Cl-4-NO$_2$—C$_6$H$_3$ |
| 246. | 2-Cl-5-NO$_2$—C$_6$H$_3$ |

TABLE 1-continued

Compounds in Table 1 are of general formula (I) wherein A is CH, B is OCH$_3$, E is —NR$^1$—C(CH$_3$)=N—, R$^1$ is H, R$^2$ is methyl and R$^3$ has the value listed.

| Compound No | R$^3$ |
| --- | --- |
| 247. | 2-Cl-6-NO$_2$—C$_6$H$_3$ |
| 248. | 3-Cl-2-NO$_2$—C$_6$H$_3$ |
| 249. | 3-Cl-4-NO$_2$—C$_6$H$_3$ |
| 250. | 3-Cl-5-NO$_2$—C$_6$H$_3$ |
| 251. | 3-Cl-6-NO$_2$—C$_6$H$_3$ |
| 252. | 4-Cl-2-NO$_2$—C$_6$H$_3$ |
| 253. | 4-Cl-3-NO$_2$—C$_6$H$_3$ |
| 254. | 2-Cl-3-CF$_3$—C$_6$H$_3$ |
| 255. | 2-Cl-4-CF$_3$—C$_6$H$_3$ |
| 256. | 2-Cl-5-CF$_3$—C$_6$H$_3$ |
| 257. | 2-Cl-6-CF$_3$—C$_6$H$_3$ |
| 258. | 3-Cl-2-CF$_3$—C$_6$H$_3$ |
| 259. | 3-Cl-4-CF$_3$—C$_6$H$_3$ |
| 260. | 3-Cl-5-CF$_3$—C$_6$H$_3$ |
| 261. | 3-Cl-6-CF$_3$—C$_6$H$_3$ |
| 262. | 4-Cl-2-CF$_3$—C$_6$H$_3$ |
| 263. | 4-Cl-3-CF$_3$—C$_6$H$_3$ |
| 264. | 2-Cl-3-Br—C$_6$H$_3$ |
| 265. | 2-Cl-4-Br—C$_6$H$_3$ |
| 266. | 2-Cl-5-Br—C$_6$H$_3$ |
| 267. | 2-Cl-6-Br—C$_6$H$_3$ |
| 268. | 3-Cl-2-Br—C$_6$H$_3$ |
| 269. | 3-Cl-4-Br—C$_6$H$_3$ |
| 270. | 3-Cl-5-Br—C$_6$H$_3$ |
| 271. | 3-Cl-6-Br—C$_6$H$_3$ |
| 272. | 4-Cl-2-Br—C$_6$H$_3$ |
| 273. | 4-Cl-3-Br—C$_6$H$_3$ |
| 274. | 2,3-(NO$_2$)$_2$—C$_6$H$_3$ |
| 275. | 2,4-(NO$_2$)$_2$—C$_6$H$_3$ |
| 276. | 2,5-(NO$_2$)$_2$—C$_6$H$_3$ |
| 277. | 2,6-(NO$_2$)$_2$—C$_6$H$_3$ |
| 278. | 3,4-(NO$_2$)$_2$—C$_6$H$_3$ |
| 279. | 3,5-(NO$_2$)$_2$—C$_6$H$_3$ |
| 280. | 2,3-(CF$_3$)$_2$—C$_6$H$_3$ |
| 281. | 2,3-(CF$_3$)$_2$—C$_6$H$_3$ |
| 282. | 2,4-(CF$_3$)$_2$—C$_6$H$_3$ |
| 283. | 2,5-(CF$_3$)$_2$—C$_6$H$_3$ |
| 284. | 3,4-(CF$_3$)$_2$—C$_6$H$_3$ |
| 285. | 3,5-(CF$_3$)$_2$—C$_6$H$_3$ |
| 286. | 2,3-(OCH$_3$)$_2$—C$_6$H$_3$ |
| 287. | 2,4-(OCH$_3$)$_2$—C$_6$H$_3$ |
| 288. | 2,5-(OCH$_3$)$_2$—C$_6$H$_3$ |
| 289. | 2,6-(OCH$_3$)$_2$—C$_6$H$_3$ |
| 290. | 3,4-(OCH$_3$)$_2$—C$_6$H$_3$ |
| 291. | 3,5-(OCH$_3$)$_2$—C$_6$H$_3$ |
| 292. | 2,3-(OCH$_3$)$_2$—C$_6$H$_3$ |
| 293. | 2,4-(OCH$_3$)$_2$—C$_6$H$_3$ |
| 294. | 2,5-(OCH$_3$)$_2$—C$_6$H$_3$ |
| 295. | 2,6-(OCH$_3$)$_2$—C$_6$H$_3$ |
| 296. | 3,4-(OCH$_3$)$_2$—C$_6$H$_3$ |
| 297. | 3,5-(OCH$_3$)$_2$—C$_6$H$_3$ |
| 298. | 2,3,4,5-F4—C$_6$H |
| 299. | 2,3,5,6-F4—C$_6$H |
| 300. | 2,3,4,6-F4—C$_6$H |
| 301. | 2,3,4,5-Cl$_4$—C$_6$H |
| 302. | 2,3,4,5-Cl$_4$—C$_6$H |
| 303. | 2,3,4,5-Cl$_4$—C$_6$H |

TABLE 2

Table 2 comprises 303 compounds of formula (I) wherein A is CH, B is OCH$_3$, E is —NR$^1$—C(CH$_3$)=N—, R$^1$ and R$^2$ are both methyl and R$^3$ is as listed for Table 1.

TABLE 3

Table 3 comprises 303 compounds of formula (I) wherein A is CH, B is NHCH$_3$, E is —NR$^1$—C(CH$_3$)=N—, R$^1$ is hydrogen, R$^2$ is methyl, and R$^5$ is as listed for Table 1.

TABLE 4

Table 4 comprises 303 compounds of formula (I) wherein A is CH, B is NHCH$_3$, E is —NR$^1$—C(CH$_3$)=N—, R$^1$ and R$^2$ are both methyl, and R$^3$ is as listed for Table 1.

TABLE 5

Table 5 comprises 303 compounds of formula (I) wherein A is NH, B is OCH$_3$, E is —NR$^1$—C(CH$_3$)=N—, R$^1$ is hydrogen, R$^2$ is methyl and R$^3$ is as listed for Table I.

TABLE 6

Table 6 comprises 303 compounds of formula (I) wherein A is NH, B is OCH$_3$, E is —NR$^1$—C(CH$_3$)=N—, R$^1$ and R$^2$ are both methyl and R$^3$ is as listed for Table I.

TABLE 7

Table 7 comprises 303 compounds of formula (I) wherein A is NH, B is NHCH$_3$, E is —NR$^1$—C(CH$_3$)=N—, R$^1$ is hydrogen, R$^2$ is methyl and R$^3$ is as listed for Table I.

TABLE 8

Table 8 comprises 303 compounds of formula (I) wherein A is NH, B is NHCH$_3$, E is —NR$^1$—C(CH$_3$)=N—, R$^1$ and R$^2$ are both methyl and R$^3$ is as listed for Table I.

TABLE 9

Table 9 comprises 303 compounds of formula (I) wherein A is CH, B is OCH$_3$, E is —NR$^1$—C(CH$_3$)=N—, R$^1$ is allyl, R$^1$ is methyl and R$^3$ is as listed for Table 1.

TABLE 10

Table 10 comprises 303 compounds of formula (I) wherein A is CH, B is OCH$_3$, E is —N=C(CH$_3$)—NR$^1$—, R$^1$ and R$^2$ are both methyl and R$^3$ is as listed for Table 1.

TABLE 11

Table 11 comprises 303 compounds of formula (I) wherein A is CH, B is NHCH$_3$, E is —N=C(CH$_3$)—NR$^1$—, R$^1$ and R$^2$ are both methyl, and R$^3$ is as listed for Table 1.

TABLE 12

Table 12 comprises 303 compounds of formula (I) wherein A is NH, B is OCH$_3$, E is —N=C(CH$_3$)—NR$^1$—, R$^1$ and R$^2$ are both methyl, and R$^3$ is as listed for Table 1.

TABLE 13

Table 13 comprises 303 compounds of formula (I) wherein A is NH, B is NHCH$_3$, E is —N=C(CH$_3$)—NR$^1$—, R$^1$ and R$^2$ are both methyl and R$^3$ is as listed for Table I.

TABLE 14

Table 14 comprises 303 compounds of formula (I) wherein A is CH, B is OCH$_3$, E is —N=C(CH$_3$)—NR$^1$—, R$^1$ is ethyl, R$^2$ is methyl and R$^3$ is as listed for Table 1.

TABLE 15

Table 15 comprises 303 compounds of formula (I) wherein A is CH, B is OCH$_3$, E is —N=C(CH$_3$)—NR$^1$—, R$^1$ is allyl, R$^2$ is methyl and R$^3$ is as listed for Table 1.

TABLE 16

Table 16 gives proton NMR data obtained at 270 MHz for certain compounds described in Tables 1 to 15. Chemical shifts are measure at 20° C. in ppm from tetramethylsilane and deuterochloroform was used as solvent, unless otherwise stated. The following abbreviations are used:

| s = singlet | d = doublet | t = triplet | dd = double doublet |
|---|---|---|---|
| m = multipet | br = broad | q = quartet | ppm = parts per million |

| Compound No. (Table) | Proton NMR Data (δ) ppm |
|---|---|
| 1(1) | 2.20(6H, s), 3.66(3H, s), 3.80(3H, s), 4.97(2H, s), 7.13–7.19(1H, m), 7.29–7.40(2H, m), 7.47–7.51(1H, m), 7.55(1H, s), 7.67–7.72(2H, m), 8.52(1H, brs) |
| 2(1) | 2.20(3H, s), 2.21(3H, s), 3.65(3H, s), 3.81(3H, s), 4.97(2H, s), 7.07–8.05(8H, m), 8.60(1H, brs). |
| 7(1) | 2.17(3H, s), 2.18(3H, s), 3.65(3H, s), 3.82(3H, s), 4.95(2H, s), 7.10–7.19(2H, m), 7.28–7.38(3H, m), 7.45–7.51(1H, m), 7.55(1H, s), 7.61–7.67(2H, m), 8.53(1H, brs) |
| 7(2) | 2.01(3H, s), 2.27(3H, s), 2.96(3H, s), 3.69(3H, s), 3.82(3H, s), 4.92(2H, s), 7.11–7.15(1H, m), 7.29–7.37(4H, m), 7.49–7.52(1H, m), 7.58(1H, s), 7.61–7.64(2H, m). |
| 7(10) | 2.21(3H, s), 2.33(3H, s), 2.12(3H, s), 3.70(3H, s), 3.83(3H, s), 4.77(2H, s), 7.16–7.20(1H, m), 7.27–7.40(4H, m), 7.48–7.53(1H, m), 7.61(1H, s), 7.76–7.79(2H, m). |
| 8(1) | 2.10(3H, s), 2.17(3H, s), 2.39(3H, s), 3.68(3H, s), 3.81(3H, s), 4.95(2H, s), 7.13–7.51(8H, m), 7.56(1H, s), 8.44(1H, brs). |
| 9(1) | 2.17(3H, s), 2.19(3H, s), 2.38(3H, s), 3.65(3H, s), 3.80(3H, s), 4.94(2H, s), 7.11–7.50(8H, m), 7.54(1H, s), 8.50(1H, brs). |
| 9(2) | 2.17(3H, s), 2.37(3H, s), 2.38(3H, s), 2.93(3H, s), 3.68(3H, s), 3.81(3H, s), 4.91(3H, s), 7.11–7.54(8H, m), 7.56(1H,s s) |
| 9(10) | 2.19(3H, s), 2.32(3H, s), 2.38(3H, s), 3.09(3H, s), 3.67(3H, s), 3.82(3H, s), 4.75(2H, s), 7.13–7.71(8H, m), 7.60(1H, s). |
| 10(1) | 2.16(3H, s), 2.17(3H, s), 2.36(3H, s), 3.64(3H, s), 3.81(3H, s), 4.94(2H, s), 7.14–7.17(3H, m), 7.30–7.35(3H, m), 7.45–7.50(1H, m), 7.53(1H, s), 7.57–7.61(2H, m), 8.50(1H, brs). |
| 18(1) | 2.12(3H, s), 2.19(3H, d), 3.68(3H, s), 3.81(3H, s), 4.96(2H, s), 6.77–6.91(2H, m), 7.13–7.19(1H, m), 7.39–7.48(2H, m), 7.46–7.58(2H, m), 7.53(1H, s), 7.57–7.61(2H, m), 8.50(1H, brs). |
| 18(9) | 1.99(3H, s), 2.20(3H, d), 3.67(3H, s), 3.79(3H, s), 3.82(3H, s), 4.89(2H, s), 5.09–5.20(2H, m), 5.87–6.01(1H, m), 6.77–6.91(2H, m), 7.10–7.16(1H, m), 7.23–7.31(2H, m), 7.42–7.48(1H, m), 7.56(1H, s), 7.55–7.62(1H, m). (Isomeric mixture). |
| 18(10) | 2.18(3H, s), 2.32(3H, d), 3.11(3H, s), 3.69(2H, s), 3.82(3H, s), 4.76(2H, S), 6.75–6.91(2H, m), 7.15–7.20(1H, m), 7.31–7.38(2H, m), 7.47–7.52(1H, m), 7.61(1H, s), 7.65–7.70(1H, m). |
| 18(14) | 1.21(3H, t), 2.19(3H, s), 2.33(3H, d), 3.65(2H, q), 3.69(3H, s), 3.82(3H, s), 3.77(2H, s), 6.75–6.91(2H, m), 7.13–7.20(1H, m), 7.31–7.39(2H, m), 7.49–7.55(1H, m), 7.61(1H, s), 7.60–7.72(1H, m). |
| 18(15) | 2.19(3H, s), 2.31(3H, d), 3.69(3H, s), 3.81(3H, s), 4.20–4.25(2H, m), 4.79(2H, s), 5.17–5.31(2H, m), 5.95–6.10(1H, m), 6.76–6.91(2H, m), 7.13–7.19(1H, m), 7.31–7.38(2H, m), 7.48–7.54(1H, m), 7.59(1H, s), 7.61–7.70(1H, m). |
| 74(1) | 2.07(3H, s), 2.09(3H, s), 3.64(3H, s), 3.79(3H, s), 4.96(2H, s), 7.14–7.34(4H, m), 7.45–7.50(1H, m), 8.55(1H, s), 7.94–8.00(1H, m), 7.51–7.55(1H, dd), 8.62(1H, brs), 9.01–9.04(1H, dd). |
| 229(1) | 2.14(3H, s), 2.19(3H, s), 3.65(3H, s), 3.81(3H, s), 4.94(2H, s), 6.97–7.49(7H, m), 7.54(1H, s), 8.42(1H, brs). |
| 229(2) | 1.99(3H, s), 2.32(3H, s), 2.97(3H, s), 3.69(3H, s), 3.80(3H, s), 4.90(2H, s), 6.96–7.53(7H, m), 7.56(1H, s). |

Compounds of formula (Ia):

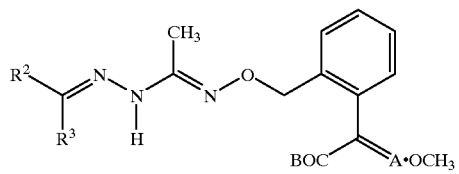

(Ia)

(that is, compounds of formula (I) wherein E is —$NR^1$—C($CH_3$)=N— and $R^1$ is hydrogen) can be prepared by reacting a compound of formula (II):

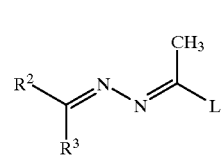

(II)

wherein $R^2$ and $R^3$ have the meanings given above and L is a leaving group, with a compound of formula (III):

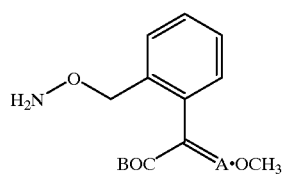

(III)

wherein A and B have the meanings given above, suitably in the presence of a base (such as triethylamine or pyridine) suitably in a convenient solvent (such as diethyl ether or tetrahydrofuran) at a temperature suitably in the range of from 20° C. to 110° C.

Compounds of formula (Ia) can exist as the tautomeric form (Ib):

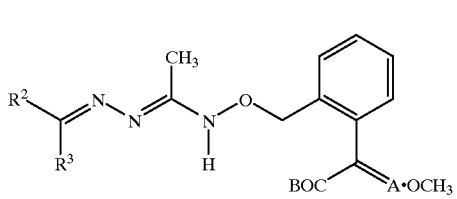

(Ib)

(that is, compounds of formula (I) wherein E is —N═C (CH$_3$)—NR$^1$—, and R$^1$ is hydrogen) and N-alkylation may give rise to a mixture of products of formula (I) where E is —NR$^1$—C(CH$_3$)═N— or —N═C(CH$_3$)—NR$^1$— and R$^1$ is alkyl. However, the unalkylated products usually exist in the form (Ia).

Thus, compounds of formula (I) wherein R$^1$ is other than hydrogen, can be prepared by reacting a compound of formula (Ia) with a compound of formula R$^1$L (wherein R$^1$ is not hydrogen) suitably in the presence of a base (such as sodium hydride, potassium carbonate or triethylarnine) suitably in a convenient solvent (such as diethyl ether or tetrahydrofuran) at a temperature suitably in the range of from 20° C. to 110° C. Where a mixture of products is obtained (ie a mixture of compounds of formula (I) where E is —NR$^1$—C(CH$_3$)═N— and —N═C(CH$_3$)—NR$^1$—), the individual components may be separated by, for example, chromatographic techniques. Examples of the L group are halogen (including bromine and iodine) and CH$_3$OSO$_2$. The L group of the compound of formula (II) may also be methoxy.

Compounds of formula (II), wherein L is other than methoxy, can be prepared by reacting a compound of formula (IV):

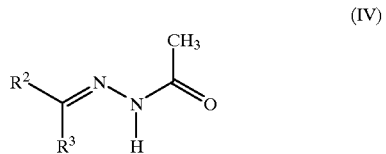

(IV)

with a halogenating agent such as phosphorus trichloride, phosphorus pentachloride, phosphorus tribromide, phosphorus pentabromide, phosphorus oxychloride or phosphorus oxybromide optionally in a convenient solvent such as tetrahydrofuran.

Compounds of formula (II), wherein L is methoxy, can be prepared by reacting a hydrazone of formula (V):

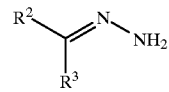

(V)

with trimethylorthoacetate in the presence of a Lewis Acid (such as zinc (II) chloride, aluminium trichloride or boron trifluoride etherate), optionally in a suitable solvent.

Compounds of formula (III) can be prepared from a compound of formula (VI):

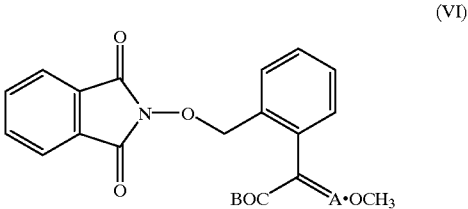

(VI)

as described in EP-A-0463488 (see Compound 22, Scheme 5, page 10).

Compounds of formula (IV) and (V) can be prepared by methods well documented in the literature. In particular, compounds of formula (V) can be prepared by reacting a ketone of formula R$^2$R$^3$C═O with hydrazine hydrate at a temperature of from 20–90° C.

In yet another aspect the present invention provides a process for the preparation of a compound of formula (I) as described above.

The compounds of formula (I) are active fungicides and may be used to control one or more of the following pathogens: *Pyricularia oryzae* on rice and wheat and other Pyricularia spp. on other hosts; *Puccinia recondita, Puccinia striiformis* and other rusts on wheat, *Puccinia hordei, Puccinia striiformis* and other rusts on barley, and rusts on other hosts e.g. turf, rye, coffee, pears, apples, peanuts, sugar beet, vegetables and ornamental plants; *Erysiphe graminis* (powdery mildew) on barley, wheat, rye and turf and other powdery mildews on various hosts such as *Sphaerotheca macularis* on hops, *Sphaerotheca fuliginea* on cucurbits (e.g. cucumber), *Podosphaera leucotricha* on apple and *Uncinula necator* on vines; Cochliobolus spp., Helminthosporium spp., Drechslera spp. (Pyrenophora spp.), Rhynchosporium spp., Septoria spp. (including *Mycosphaerella graminicola* and *Leptosphaeria nodorum*), *Pseudocercosporella herpotrichoides* and *Gaeumannomyces graminis* on cereals (e.g. wheat, barley, rye), turf and other hosts; *Cercospora arachidicola* and *Cercosporidium personatum* on peanuts and other Cercospora species on other hosts, for example, sugar beet, bananas, soya beans and rice; *Botrytis cinerea* (grey mould) on tomatoes, strawberries, vegetables, vines and other hosts and other Botrytis spp. on other hosts; Alternaria spp. on vegetables (e.g. cucumber), oil-seed rape, apples, tomatoes, cereals (e.g. wheat) and other hosts; Venturia spp. (including *Venturia inaequalis* (scab)) on apples, pears, stone fruit, tree nuts and other hosts; Cladosporium spp. on a range of hosts including cereals (e.g. wheat); Monilinia spp. on stone fruit, tree nuts and other hosts; Didymella spp. on tomatoes, turf, wheat and other hosts; Phoma spp. on oil-seed rape, turf, rice, potatoes, wheat and other hosts; Aspergillus spp. and Aureobasidium spp. on wheat, lumber and other hosts; Ascochyta spp. on peas, wheat, barley and other hosts; *Plasmopara viticola* on vines; other downy mildews such as *Bremia lactucae* on lettuce, Peronospora spp. on soybeans, tobacco, onions and other hosts, *Pseudoperonospora humuli* on hops and *Pseudoperonospora cubensis* on cucurbits; Pythium spp. (including *Pythium ultimum*) on turf and other hosts; *Phytophthora infestans* on potatoes and tomatoes and other Phytophthora spp. on vegetables, strawberries, avocado, pepper, ornamentals, tobacco, cocoa and other hosts; *Thanatephorus cucumeris* on rice and turf and other Rhizoctonia species on various hosts such as wheat and barley, vegetables, cotton and turf; Sclerotinia spp. on turf, peanuts, oil-seed rape and other hosts; Sclerotium spp. on turf, peanuts and other hosts; Colletotrichum spp. on a range of hosts including turf, coffee and vegetables; *Laetisaria fuciformis* on turf; Mycosphaerella spp. on banana, peanut, citrus, pecan, papaya and other hosts; Diaporthe spp. on citrus, soybean, melon, pear, lupin and other hosts; Elsinoe spp. on citrus, vines, olives, pecans, roses and other hosts; Pyrenopeziza spp. on oil-seed rape and other hosts; *Oncobasidium theobromae* on cocoa causing vascular streak dieback; Fusarium spp., Typhula spp., *Microdochium nivale*, Ustilago spp., Urocystis spp., Tilletia spp., and *Claviceps purpurea* on a variety of hosts but particularly wheat, barley, turf and maize; Ramularia spp. on sugar beet and other hosts; post-harvest diseases particularly of fruit (e.g. *Pencilium digitatum* and *P. italicum* and *Trichoderma viride* on oranges, *Colletotrichum musae* and *Gloeosporium musarum* on bananas and *Botrytis cinerea* on grapes); other pathogens on vines, notably *Eutypa lata, Guignardia bidwellii, Phellinus igniarus, Phomopsis viticola, Pseudopezicula tracheiphila* and *Stereum hirsutum*; other pathogens on lumber, notably *Cephaloascus fragrans,* Ceratocystis spp., *Ophiostoma piceae*, Penicillium spp., *Trichoderma pseudokoningii, Trichoderma viride, Trichoderma harzianum, Aspergillus niger, Leptographium lindbergi* and *Aureobasidium pullulans*; and fungal vectors of viral diseases e.g. *Polymyxa graminis* on cereals as the vector of barley yellow mosaic virus (BYMV).

Further, some of the compounds may be useful as seed dressings against pathogens including Fusarium spp., Septoria spp., Tilletia spp., (e.g. bunt, a seed-borne disease of wheat), Ustilago spp. and Helminthosporium spp. on cereals, *Rhizoctonia solani* on cotton and *Pyricularia oryzae* on rice. In particular, some of the compounds show good eradicant activity against *Plasmopara viticola* and *Pythium ultimum.*

The compounds may move acropetally/locally in plant tissue. Moreover, the compounds may be volatile enough to be active in the vapour phase against fungi on the plant.

The invention therefore provides a method of combating fungi which comprises applying to a plant, to a seed of a plant or to the locus of the plant or seed a fungicidally effective amount of a compound as hereinbefore defined, or a composition containing the same.

The compounds may be used directly for agricultural purposes but are more conveniently formulated into compositions using a carrier or diluent. The invention thus provides fungicidal compositions comprising a compound as hereinbefore defined and an acceptable carrier or diluent therefor. It is preferred that all compositions, both solid and liquid formulations, comprise 0.0001 to 95%, more preferably 1 to 85%, for example 1 to 25% or 25 to 60%, of a compound as hereinbefore defined.

When applied to the foliage of plants, the compounds of the invention are applied at rates of 0.1 g to 10 kg, preferably 1 g to 8 kg, more preferably 10 g to 4 kg, of active ingredient (invention compound) per hectare.

When used as seed dressings, the compounds of the invention are used at rates of 0.0001 g (for example 0.001 g or 0.05 g) to 10 g, preferably 0.005 g to 8 g, more preferably 0.005 g to 4 g, of active ingredient (invention compound) per kilogram of seed.

The compounds can be applied in a number of ways. For example, they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules.

Application can be to any part of the plant including the foliage, stems, branches or roots, or to soil surrounding the roots, or to the seed before it is planted, or to the soil generally, to paddy water or to hydroponic culture systems. The invention compounds may also be injected into plants or sprayed onto vegetation using electrodynamic spraying techniques or other low volume methods, or applied by land or aerial irrigation systems.

The term "plant" as used herein includes seedlings, bushes and trees. Furthermore, the fungicidal method of the invention includes preventative, protectant, prophylactic, systemic, curative and eradicant treatments.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example, fillers such as kaolin, bentonite, kieselguhr, dolomite, calcium carbonate, talc, powdered magnesia, fuller's earth, gypsum, diatomaceous earth and china clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example, a mineral oil) for assisting the adhesion of the composition to the seed; alternatively the active ingredient can be formulated for seed dressing purposes using an organic solvent (for example, N-methylpyrrolidone, propylene glycol or N,N-dimethylformamide). The compositions may also be in the form of water dispersible powders or water dispersible granules comprising wetting or dispersing agents to facilitate the dispersion in liquids. The powders and granules may also contain fillers and suspending agents.

The compositions may also be in the form of soluble powders or granules, or in the form of solutions in polar solvents.

Soluble powders may be prepared by mixing the active ingredient with a water-soluble salt such as sodium bicarbonate, sodium carbonate, magnesium sulphate or a polysaccharide, and a wetting or dispersing agent to improve water dispersibility/solubility. The mixture may then be ground to a fine powder. Similar compositions may also be granulated to form water-soluble granules. Solutions may be prepared by dissolving the active ingredient in polar solvents such as ketones, alcohols and glycol ethers. These solutions may contain surface active agents to improve water dilution and prevent crystallisation in a spray tank.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as cyclohexanone and methylcyclohexanone, chlorinated hydrocarbons such as chlorobenzene and trichlorethane, and alcohols such as benzyl alcohol, furfuryl alcohol, butanol and glycol ethers.

Aqueous suspension concentrates of largely insoluble solids may be prepared by ball or bead milling with a dispersing agent with a suspending agent included to stop the solid settling.

Compositions to be used as sprays may be in the form of aerosols wherein the formulation is held in a container under pressure of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the uptake, distribution, adhesive power and resistance to rain on treated surfaces, the different compositions can be better adapted for various utilities. Other additives may be included to improve the biological efficacy of the various formulations. Such additives can be surface active materials to improve the wetting and retention on surfaces treated with the formulation and also the uptake and mobility of the active material, or additionally can include oil based spray additives, for example, certain mineral oil and natural plant oil (such as soya bean and rape seed oil) additives, or blends of them with other adjuvants.

The invention compounds can be used as mixtures with fertilisers (e.g. nitrogen-, potassium- or phosphorus-containing fertilisers). Compositions comprising only granules of fertiliser incorporating, for example coated with, a compound of formula (I) are preferred. Such granules suitably contain up to 25% by weight of the compound. The invention therefore also provides a fertiliser composition comprising a fertiliser and the compound of general formula (I) or a salt or metal complex thereof.

Water dispersible powders, emulsifiable concentrates and suspension concentrates will normally contain surfactants, e.g. a wetting agent, dispersing agent, emulsifying agent or suspending agent. These agents can be cationic, anionic or non-ionic agents.

Suitable cationic agents are quaternary ammonium compounds, for example, cetyltrimethylammonium bromide. Suitable anionic agents are soaps, salts of aliphatic monoesters of sulphuric acid (for example, sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and tri-isopropylnaphthalene sulphonates).

Suitable non-ionic agents are the condensation products of ethylene oxide with fatty alcohols such as oleyl or cetyl alcohol, or with alkyl phenols such as octyl- or nonyiphenol and octylcresol. Other non-ionic agents are the partial esters derived from long chain fatty acids and hexitol anhydrides, alkyl glucosides, polysaccharides and the lecithins and the condensation products of the said partial esters with ethylene oxide. Suitable suspending agents are hydrophilic colloids (for example, polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use, these concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 1–85%, for example 1–25% or 25–60%, by weight of the active ingredient. After dilution to form aqueous preparations, such preparations may contain varying amounts of the active ingredient depending upon the intended purpose, but an aqueous preparation containing 0.0001 to 10%, for example 0.005 to 10%, by weight of active ingredient may be used.

The compositions of this invention may contain other compounds having biological activity, e.g. compounds having similar or complementary fungicidal activity or which possess plant growth regulating, herbicidal or insecticidal activity.

By including another fungicide, the resulting composition can have a broader spectrum of activity or a greater level of intrinsic activity than the compound of general formula (I) alone. Further the other fungicide can have a synergistic effect on the fungicidal activity of the compound of general formula (I). Examples of fungicidal compounds which may be included in the composition of the invention are (E)-N-methyl-2-(2-phenoxyphenyl)-2-methoxyiminoacetamide, (E)-N-methyl-2-[2-(2,5-dimethylphenoxymethyl)phenyl]-2-methoxy-iminoacetamide, (RS)-1-aminopropylphosphonic acid, (RS)-4-(4-chlorophenyl)-2-phenyl-2-(1H-1,2,4-triazol-1-ylmethyl)butyronitrile, Z)-N-but-2-enyloxymethyl-2-chloro-2',6'-diethylacetanilide, 1-(2-cyano-2-methoxyiminoacetyl)-3-ethyl urea, 4-(2,2-difluoro-1,3-benzodioxol-4-yl)pyrrole-3-carbonitrile, 4-bromo-2-cyano-N,N-dimethyl-6-trifluoromethylbenzimidazole-1-sulphonamide, 5-ethyl-5,8-dihydro-8-oxo(1,3)-dioxol-(4,5-g)quinoline-7-carboxylic acid, α-[N-(3-chloro-2,6-xylyl)-2-methoxyacetamido]-γ-butyrolactone, N-(2-methoxy-5-pyridyl)-cyclopropane carboxamide, alanycarb, aldimorph, ampropylfos, anilazine, azaconazole, azoxystrobin, benalaxyl, benomyl, biloxazol, binapacryl, bitertanol, blasticidin S, bromuconazole, bupirimate, butenachlor, buthiobate, captafol, captan, carbendazim, carbendazim chlorhydrate, carboxin, chinomethionate, chlorbenzthiazone, chloroneb, chlorothalonil, chlorozolinate, clozylacon, copper containing compounds such as copper oxychloride, copper oxyquinolate, copper sulphate, copper tallate, and Bordeaux mixture, cycloheximide, cymoxanil, cyproconazole, cyprofuram, debacarb, di-2-pyridyl disulphide 1,1'-dioxide, dichlofluanid, dichlone, diclobutrazol, diclomezine, dicloran, didecyl dimethyl ammonium chloride, diethofencarb, difenoconazole, diflumetorim, O,O-di-iso-propyl-S-benzyl thiophosphate, dimefluazole, dimetconazole, dimethomorph, dimethirimol, diniconazole, dinocap, dipyrithione, ditalimfos, dithianon, dodemorph, dodine, doguadine, edifenphos, epoxiconazole, etaconazole, ethirimol, ethoxyquin, ethyl (Z)-N-benzyl-N-([methyl (methylthioethylideneamino-oxycarbonyl)amino]thio)-β-alaninate, etridiazole, fenaminosulph, fenapanil, fenarimol, fenbuconazole, fenfuram, fenpiclonil, fenpropidin, fenpropimorph, fentin acetate, fentin hydroxide, ferbam, ferimzone, fluazinam, fludioxonil, fluoroimide, fluquinconazole, flusilazole, flutolanil, flutriafol, folpet, fuberidazole, furalaxyl, furametpyr, furconazole-cis, guazatine, hexaconazole, hydroxyisoxazole, hymexazole, imazalil, imibenconazole, iminoctadine albesilate, ipconazole, iprobenfos, iprodione, isopropanyl s butyl carbamate, isoprothiolane, kasugamycin, kresoxim-methyl, KTU3616, mancozeb, maneb, mepanipyrim, mepronil, metalaxyl, metconazole, methfuroxam, metiram, metiram-zinc, metsulfovax, MON41100, myclobutanil, NTN0301, neoasozin, nickel dimethyldithiocarbamate, nitrothal-isopropyl, nuarimol, ofurace, organomercury compounds, oxadixyl, oxolinic acid, oxycarboxin, pefurazoate, penconazole, pencycuron, phenazin oxide, phosetyl-Al, phosphorus acids, phthalide, polyoxin D, polyram, probenazole, prochloraz, procymidone, propamocarb, propanocarb hydrochloride, propiconazole, propineb, propionic acid, prothiocarb, pyracarbolid, pyrazophos, pyrifenox, pyrimethanil, pyroquilon, pyroxyfur, pyrrolnitrin, quaternary ammonium compounds, quinconazole, quinomethionate, quinoxyfen, quintozene, rabenazole, sodium pentachlorophenate, spiroxamine, streptomycin, sulphur, tebuconazole, techlofthalam, tecnazene, tetraconazole, thiabendazole, thicyofen, thifluzamide, 2-(thiocyanomethylthio)benzothiazole, thiophanatemethyl, thiram, timibenconazole, tolclofos-methyl, tolylfluanid, triacetate salt of 1,1'-iminodi(octamethylene)diguanidine, triadimefon, triadimenol, triazbutyl, triazoxide, tricyclazole, tridemorph, triforine, triflumizole, triticonazole, validamycin A, vapam, vinclozolin, XRD-563, zineb and ziram. The compounds of general formula (I) can be mixed with soil, peat or other rooting media for the protection of plants against seed-borne, soil-borne or foliar fungal diseases.

The following Examples illustrate the invention. Throughout the Examples, the term 'ether' refers to diethyl ether, magnesium sulphate was used to dry solutions except where otherwise indicated, and solutions were concentrated under reduced pressure. All reactions were performed under an atmosphere of nitrogen and solvents were dried before use, where appropriate. Unless otherwise stated, chromatography was performed on a column of silica gel as the stationary phase. The following abbreviations are used throughout:

| | |
|---|---|
| m.p. = melting point | THF = tetrahydrofuran |
| DMF = N,N-dimethylformamide | HPLC = High performance liquid chromatography |

EXAMPLE 1

This Example illustrates the preparation of (E), (E)-methyl 2-[2-(phenylacethydrazono-acetoximinomethylphenyl]-3-methoxypropenoate (Compound No. 1 of Table 1).

Stage 1

A two phase mixture of acetophenone (5.00 g) and hydrazine hydrate (4.17 g) was heated for 10 hours at 60° C. The mixture was cooled at 20° C., poured into water and extracted with ether. The ethereal extracts were washed with water, dried and the solvent removed to give a crude oil which was purified by flash column chromatography using silica-gel eluted with ether:hexane 1:1 and 2:1, to give phenylacetylhydrazone (3.30 g, 54%) as a yellow oil.

Stage 2

A solution of phenylacetylhydrazone (1.5 g) and zinc (II) chloride (0.2 g) in trimethylorthoacetate (10 ml) was stirred at 20° C. for two hours. This solution was poured directly onto a silica-gel chromatography column (hexane:ether 20:1 as eluent) to give the crude imidate as a yellow oil (0.501 g, 24%).

Stage 3

(E)-methyl 2-[phthalimidooxymethylphenyl]-3-methoxypropenoate (0.80 g) (prepared as described in Example 4 of EP-A-0463488) was suspended in methanol (8 ml) at room temperature. Hydrazine hydrate (0.109 g) was added to the suspension and the resulting solution stirred for 2½ hours. The imidate from stage 2 (0.40 g) in methanol (2 ml) and pyridine (2 drops) were added and the resultant solution sitrred for 5 hours and left to stand overnight. The white precipitate which formed was filtered off and the solvent removed to give a yellow gum. This was purified by flash column chromatography, using silica-gel and hexane:ether 2:1 as eluent to give the crude product. HPLC (0.5% THF in $CH_2Cl_2$ as eluent) was performed on this material to give the desired product as a white solid (0.082 g, 10%):m.p. 118–118.5; (NMR data given in Table 16).

EXAMPLE 2

This Example illustrates the preparation of the compounds of formula (I) where A is CH, B is $OCH_3$, $R^2$ is $CH_3$, $R^3$ is 2-thienyl and E is (i) —NH—C($CH_3$)=N— and (ii) —N($CH_3$)—C($CH_3$)=N—(Compounds Nos 229 of Table 1 and 229 of Table 2).

Stage 1

A two phase mixture of 2-acetylthiophene (21.0 g) and hydrazine hydrate (35 g) was heated for 7½ hours at 60° C. The mixture was cooled to 20° C., poured into water and extracted with ether. The ethereal extracts were washed with water, dried and the solvent removed to give thienylacetylhydrazone as a yellow solid (23.2 g, 99%).

Stage 2

A solution of thienylacetylhydrazone (15.0 g) and zinc (II) chloride (1.0 g) in trimethylorthoacetate (100 ml) was stirred at 20° C. for 4 hours. The solution was poured into water and extracted with ether. The ethereal extracts were dried and the solvent removed to give the imidate as a yellow gum (18.1 g, 86%).

Stage 3

(E)-methyl-2-[phthalimidooxymethylphenyl]-3-methoxypropenoate (6.0 g) (prepared as described in Example 4 of EP-A-0463488) was suspended in methanol (40 ml) at room temperature. Hydrazine hydrate (1.0 g) was added to the suspension and the resulting solution stirred for 2½ hours. The imidate from stage 2 (6.4 g) and pyridine (2 drops) were added and the resultant solution stirred for 1½ hours. The solution was left to stand overnight. The white precipitate which formed was filtered off and the solvent removed to give a yellow gum. This was purified by flash column chromatography, using silica gel and ethyl acetate::hexane 1:3 as eluent to give a crude product. HPLC (1% THF in $CH_2Cl_2$ as eluent) was performed on the crude product to give the desired material (Compound No. 229 of Table 1) as a yellow solid (0.196 g, 3%); (NMR data given in Table 16).

Stage 4

Sodium hydride (60%) (0.163 g) was washed with hexane and suspended in dry DMF (2 ml). A solution of the product from stage 3 (0.3 g) and methyl iodide (1.25 g) in DMF (3 ml) was added at 0° C. and then warmed to 20° C. The reaction mixture was poured into water and extracted with ether. The ethereal extracts were washed with water, dried and the solvent removed to give a crude oil which was purified by flash column chromatography, using silica gel and hexane:ether 2:3 as eluent to give a crude product. HPLC (hexane:ether 2:3 as eluent) was performed on the crude product to give the desired material (Compound No. 229 of Table 2) as a yellow gum (0.055 g, 18%); (NMR data given in Table 16).

EXAMPLE 3

This Example illustrates the preparation of the compounds of formula (I) where A is CH, B is OCH$_3$, R$^2$ is CH$_3$, R$^3$ is 2,4-difluorophenyl and E is (i) —NH—C(CH$_3$)=N—, (ii) —N(allyl)—C(CH$_3$)=N— and (iii) —N=C(CH$_3$)—N(allyl)— (Compounds Nos 18 of Table 1, 18 of Table 9 and 18 of Table 15).

Stage 1

A two phase mixture of 2,4-difluoroacetophenone (19.3 g), hydrazine hydrate (12.4 ml) and water (5 ml) was heated for 10 hours at 60° C. The mixture was cooled to 200C, poured into water and extracted with ether. The ethereal extracts were washed with water, dried and the solvent removed to give 2,4-difluorophenylacetylhydrazone as a yellow oil (14.7 g, 70%).

Stage 2

A solution 2,4-difluorophenylacetylhydrazone (15.5 g) and zinc (II) chloride (1.0 g) in trimethylorthoacetate (100 ml) was stirred at 20° C. for 4 hours. The crude product was transferred directly onto a silica gel flash chromatography column to give the imidate as a yellow oil (9.0 g, 44%).

Stage 3

E-methyl-2-[phthalimidooxymethylphenyl]-3-methoxypropenoate (10.1 g) (prepared as described in Example 4 of EP-A-0463488) was suspended in methanol (80 ml) at room temperature. Hydrazine hydrate (1.38 g) was added to the suspension and the resulting solution stirred for 2½ hours. The imidate from stage 2 (6.2 g) and pyridine (0.2 ml) were added and the resultant solution stirred for 1½. hours. The solution was left to stand overnight. The white precipitate which formed was filtered off and the solvent removed to give a yellow gum. This was purified by flash column chromatography, using silica gel and hexane/ether 2:1 as eluent to give a crude product. HPLC (0.2 and 0.5% THF in methylene chloride as eluent) was performed on the crude product to give the desired material (Compound 18 of Table I) as a clear gum (2.99 g, 25%); (NMR data given in Table 16).

Stage 4

Sodium hydride (60%) (0.066 g) was washed with hexane and suspended in dry DMF (2 ml). A solution of the product from stage 3 (0.647 g) and allyl bromide (0.27 g) in DMF (13 ml) was added at 0° C. and then warmed to 20° C. The reaction mixture was poured into water and extracted with ether. The ethereal extracts were washed with water, dried and the solvent removed to give a crude oil which was purified twice by flash column chromatography using silica gel and hexane:ether 3:2 and 0.5% THF in methylene chloride as eluents to give Compound 18 of Table 9 (0.048 g, 7%) and Compound 18 of Table 15 (0.027 g, 4%), both as yellow gums; (NMR data given in Table (16).

EXAMPLE 4

The compounds were tested against a variety of foliar fungal diseases of plants. The technique employed was as follows.

The plants were grown in John Innes Potting Compost (No 1 or 2) in 4 cm diameter minipots. The test compounds were formulated either by bead milling with aqueous DISPERSOL T or as a solution in acetone or acetone/ethanol which was diluted to the required concentration immediately before use. The formulations (100 ppm active ingredient) were sprayed on to the foliage or applied to the roots of the plants in the soil. The sprays were applied to maximum retention and the root drenches to a final concentration equivalent to approximately 40 ppm a.i. in dry soil. TWEEN 20 was added to give a final concentration of 0.1% by volume when the sprays were applied to cereals. For most of the tests the compounds were applied to the soil (roots) or to the foliage (by spraying) one or two days before the plant was inoculated with the disease. Exceptions were the test on *Erysiphe graminis* in which the plants were inoculated 24 hours before treatment and the test on *Puccinia recondita* in which the plants were inoculated 48 hours before treatment. Foliar pathogens were applied as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease level present (i.e. leaf area covered by actively sporulating disease) on each of the treated plants was recorded using the following assessment scale:

0 = 0% disease present
1 = 0.1–1% disease present
3 = 1.1–3% disease present
5 = 3.1–5% disease present
10 = 5.1–10% disease present
20 and 24 = 10.1–20% disease present
30 = 20.1–30% disease present
60 = 30.1–60% disease present
90 and 94 = 60.1–100% disease present Each assessment was then expressed as a percentage of the level of disease present on the untreated control plants. This calculated value is referred to as a POCO (Percentage of Control) value. An example of a typical calculation is as follows:

Disease level on untreated control=90

Disese level on treated plant=30

POCO=disease level on treated plant×100=×100=33.3 disease level on untreated control 90

This calculated POCO value is then rounded to the nearest of the values in the 9-point assessment scale shown above. In this particular example, the POCO value would be rounded to 30. If the calculated POCO falls exactly mid-way between two of the points, it is rounded to the lower of the two values.

The results are shown in Table 17.

TABLE 17

| Compound No. (Table No.) | ERYSGT | LEPTNO | PUCCRT | PLASVI | PHYTIN | BOTRCI | VENTIN |
|---|---|---|---|---|---|---|---|
| 1(1) | 0 | 5 | 90 | 0 | 10 | 20 | 0 |
| 2(1) | 0 | 90 | 5 | 0 | 90 | 30 | 0 |
| 7(1) | 0 | 30 | 90 | 0 | 60 | 5 | 0 |

TABLE 17-continued

| Compound No. (Table No.) | ERYSGT | LEPTNO | PUCCRT | PLASVI | PHYTIN | BOTRCI | VENTIN |
|---|---|---|---|---|---|---|---|
| 7(2) | 0 | 60 | 90 | 60 | 60 | 30 | 5 |
| 8(1) | 0 | 90 | 10 | 0 | 0 | 90 | 0 |
| 9(1) | 10 | 90 | 0 | 0 | 30 | 0 | 0 |
| 9(2) | 90 | 5 | 90 | 60 | 60 | 30 | 5 |
| 10(1) | 1 | 90 | 90 | 0 | 5 | 0 | 0 |
| 21(1) | 0 | 30 | 20 | 0 | 0 | 60 | 0 |
| 21(9) | 30 | 90 | 90 | 0 | 60 | 30 | 5 |
| 74(1) | 90 | 60 | 60 | 0 | 90 | 0 | 10 |
| 229(1) | 90 | 90 | 90 | 0 | 60 | 60 | 0 |
| 229(2) | 60 | 20 | 60 | 0 | 10 | 90 | 0 |

Unless stated otherwise, data represent activity following application as a combined foliar spray and root drench treatment at 100 ppm.

| Key to Diseases | |
|---|---|
| ERYSGT | *Erysiphe graminis f. sp. tritici* (Wheat powdery mildew) |
| PLASVI | *Plasmopara viticola* (vine downy mildew) |
| LEPTNO | *Septoria nodorum* (wheat glume blotch) |
| PHYTIN | *Phytophthora infestans lycopersici* (late blight on tomatoes) |
| PUCCRT | *Puccinia recondita* (wheat brown rust) |
| VENTIN | *Venturia inaequalis* (apple scab) |
| BOTRCI | *Botrytis cinerea* (grey mould) |

What is claimed is:

1. A compound having the general formula (I):

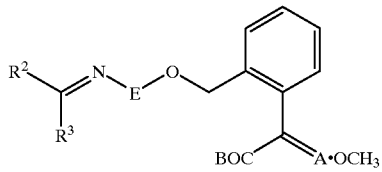

(I)

or a stereoisomer thereof, wherein A is CH or N, B is $OCH_3$ or $NHCH_3$, E is $-NR^1-C(CH_3)=N-$, $-N=C(CH_3)-NR^1-$, $R^1$ is H, $C_{1-4}$ alkyl, $C_{2-4}$ alkenyl, $C_{2-4}$ alkynyl or optionally substituted benzyl, $R^2$ is H, $C_{1-4}$ alkyl, halo($C_{1-4}$) alkyl, $C_{3-6}$ cycloalkyl, $C_{2-4}$ alkenyl or $C_{2-4}$ alkynyl, and $R^3$ is optionally substituted aryl or optionally substituted heterocyclyl.

2. A compound according to claim 1 wherein $R^1$ is H or methyl and $R^2$ is H, methyl or cyclopropyl.

3. A compound according to claim 1 wherein A is N and B is $OCH_3$ or $NHCH_3$.

4. A compound according to claim 1 wherein A is CH and B is $OCH_3$.

5. A compound according to claim 1 wherein A is CH, B is $OCH_3$, $R^1$ is H or $CH_3$, $R^2$ is $CH_3$ and $R^3$ is phenyl substituted with halogen, $C_{1-4}$ alkyl, $C_{2-4}$ alkenyl, $C_{2-4}$ alkynyl, $C_{1-4}$ alkoxy, $C_{2-4}$ alkenyloxy, $C_{1-4}$ alkynyloxy, halo($C_{1-4}$)alkyl, halo($C_{1-4}$)alkoxy, $C_{1-4}$ alkoxy($C_{1-4}$)alkyl, acyloxy, nitro, $-NR'R''$, $-NHCOR'$, $-CONR'R''$ or $COR'$ in which R' and R'' are independently hydrogen, $C_{1-4}$ alkyl or $C_{1-4}$alkoxy.

6. A compound according to claim 1 wherein A is CH, B is $OCH_3$, $R^1$ is H or $CH_3$, $R^2$ is $CH_3$ and $R^3$ is phenyl optionally substituted with halogen, $C_{1-4}$ alkyl, halo($C_{1-4}$) alkyl, $C_{1-4}$ alkoxy, halo($C_{1-4}$)alkoxy or nitro.

7. A process for preparing a compound according to claim 1 wherein $R^1$ is H, which comprises reacting a compound of formula (II):

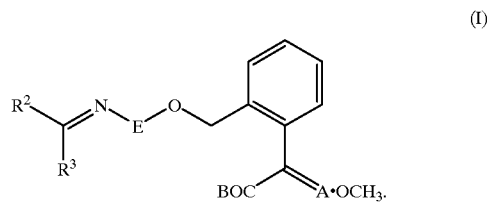

(I)

wherein $R^2$ and $R^3$ have the meanings given in claim 1 and L is a leaving group, with a compound of formula (III):

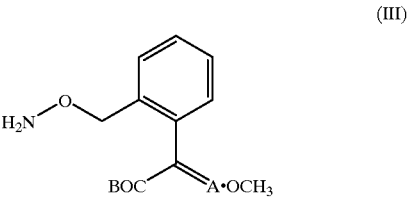

(III)

wherein A and B have the meanings given in claim 1.

8. A process for preparing a compound according to claim 1 wherein $R^1$ is other than H, which comprises reacting a compound of formula (I) as defined in claim 1 wherein $R^1$ is H, with a compound of formula $R^1L$, wherein $R^1$ is $C_{1-4}$ alkyl, $C_{2-4}$ alkenyl, $C_{2-4}$ alkynyl or optionally substituted benzyl and L is a leaving group.

9. A fungicidal composition comprising a fungicidally effective amount of a compound according to claim 1 and a fungicidally acceptable carrier or diluent therefor.

10. A method of combating fungi which comprises applying to plants, to the seeds of plants or to the locus of the plants or seeds, a compound according to claim 1.

11. A method of combating fungi which comprises applying to plants, to the seeds of plants or to the locus of the plants or seeds, a composition according to claim 9.

* * * * *